United States Patent
Kuzelka (10) Patent No.: US 10,835,185 B2
(45) Date of Patent: Nov. 17, 2020

(54) SYSTEM AND METHOD FOR DETECTING VENTILATOR-ASSOCIATED PNEUMONIA (VAP)

(71) Applicant: GENERAL ELECTRIC COMPANY, Schenectady, NY (US)

(72) Inventor: Russell James Kuzelka, McFarland, WI (US)

(73) Assignee: General Electric Company, Schenectady, NY (US)

(*) Notice: Subject to any disclaimer, the term of this patent is extended or adjusted under 35 U.S.C. 154(b) by 334 days.

(21) Appl. No.: 15/915,887

(22) Filed: Mar. 8, 2018

(65) Prior Publication Data

US 2019/0274633 A1 Sep. 12, 2019

(51) Int. Cl.
| | |
|---|---|
| A61B 5/00 | (2006.01) |
| A61B 5/08 | (2006.01) |
| A61B 6/00 | (2006.01) |
| G16H 50/20 | (2018.01) |
| A61M 16/10 | (2006.01) |

(Continued)

(52) U.S. Cl.
CPC ............ *A61B 5/7275* (2013.01); *A61B 5/082* (2013.01); *A61B 5/4848* (2013.01); *A61B 5/746* (2013.01); *A61B 6/5217* (2013.01); *G16H 50/20* (2018.01); *A61M 16/024* (2017.08); *A61M 16/0434* (2013.01); *A61M 16/104* (2013.01); *A61M 2205/7518* (2013.01)

(58) Field of Classification Search
None
See application file for complete search history.

(56) References Cited

U.S. PATENT DOCUMENTS

| | | | |
|---|---|---|---|
| 5,159,928 A * | 11/1992 | Keppel | A61M 21/00 128/905 |
| 5,996,586 A | 12/1999 | Phillips | |
| 6,312,390 B1 | 11/2001 | Phillips | |

(Continued)

FOREIGN PATENT DOCUMENTS

| | | |
|---|---|---|
| CN | 2430111 Y | 5/2001 |
| WO | 1994004705 A1 | 3/1994 |

(Continued)

OTHER PUBLICATIONS

Filipiak, Wojciech, et al. "Molecular analysis of volatile metabolites released specifically by *Staphylococcus aureus* and *Pseudomonas aeruginosa*." BMC microbiology 12.1 (2012): 113. (Year: 2012).*

(Continued)

*Primary Examiner* — Jacqueline Cheng
*Assistant Examiner* — Jairo H Portillo (57) ABSTRACT

System and methods for detecting precursors of VAP in a patient being ventilated. An exemplary method comprises obtaining a baseline value for a content of a particular VOC in tVOCs in exhaled breath of the patient being ventilated, trending changes of values of the content of the particular VOC in the tVOCs measured at various points of time after ventilation compared to the baseline value, determining whether the patient has potentially infected VAP based at least in part on the trending, and in response to determining that the patient has potentially infected the VAP, generating an alert.

18 Claims, 7 Drawing Sheets

(51) Int. Cl.
  *A61M 16/00* (2006.01)
  *A61M 16/04* (2006.01)

(56) References Cited

U.S. PATENT DOCUMENTS

| | | | |
|---|---|---|---|
| 2004/0006257 A1* | 1/2004 | Burch | A61B 5/00 600/300 |
| 2007/0281319 A1* | 12/2007 | Kolopp-Sarda | G01N 33/6893 435/7.1 |
| 2013/0261488 A1* | 10/2013 | Orr | A61B 5/0816 600/532 |
| 2015/0019257 A1* | 1/2015 | Doyle | G16H 50/20 705/3 |
| 2015/0257654 A1* | 9/2015 | Bennett-Guerrero | A61B 5/1121 600/301 |
| 2019/0006041 A1* | 1/2019 | Chiofolo | G16H 50/70 |
| 2019/0167152 A1* | 6/2019 | Weda | A61B 5/083 |

FOREIGN PATENT DOCUMENTS

| | | |
|---|---|---|
| WO | 1995033848 A1 | 12/1995 |
| WO | 1998029563 A1 | 7/1998 |
| WO | 2000057182 A1 | 9/2000 |
| WO | 2001014555 A1 | 3/2001 |
| WO | 2006085648 A1 | 8/2006 |
| WO | 2008003797 A1 | 1/2008 |
| WO | 2008021617 A1 | 2/2008 |
| WO | 2010133714 A1 | 11/2010 |
| WO | 2011003922 A1 | 1/2011 |
| WO | 2012122128 A2 | 9/2012 |

OTHER PUBLICATIONS

Golia, Saroj, K. T. Sangeetha, and C. L. Vasudha. "Microbial profile of early and late onset ventilator associated pneumonia in the intensive care unit of a tertiary care hospital in Bangalore, India." Journal of clinical and diagnostic research: JCDR 7.11 (2013): 2462. (Year: 2013).*

Schnabel et al., "Analysis of volatile organic compounds in exhaled breath to diagnose ventilator-associated pneumonia," Scientific Reports, 5:17179 | DOI: 10.1038/srep17179, 2015, 10 pages.

Fenske et al., "Human Breath Emissions of VOCs," Journal of the Air & Water Management Association, ISSN: 1096-2247 (Print) 2162-2906 (Online) Journal homepage: http://www.tandfonline.com/loi/uawm20, 2011, 6 pages.

Manzano et al., "Positive-end expiratory pressure reduces incidence of ventilator-associated pneumonia in nonhypoxemic patients," Crit Care Med., 36(8):2225-31. doi: 10.1097/CCM.0b013e31817b8a92, 2008, 2 pages.

Sethi et al., "Clinical Application of Volatile Organic Compound Analysis for Detecting Infectious Diseases," CMR Journals ASM.org, Clinical Microbiology Reviews, vol. 26, No. 3, 14 pages.

Lorente et al., "Continuous endotracheal tube cuff pressure control system protects against ventilator-associated pneumonia," Critical Care, 18 :R77, http://ccforum.com/content/18/2/R77, 2014, 8 pages.

Kollef et al., "Economic impact of ventilator-associated pneumonia in a large matched cohort," Infect Control Hosp Epidemiol, 33(3):250-6. doi: 10.1086/664049, 2012, 2 pages.

Ioanes et al., "Microbial investigaion in ventilator-associated pneumonia," ERS Journals Ltd 2001, European Respiratory Journal ISSM 0903-1936, 2001, 11 pages.

Grgurich et al., "Management and Prevention of Ventilator-associated Pneumonia Caused by Multidrug-resistant Pathogens," Expert Rev Resp Med., https://www.medscape.com/viewarticle/774933, 2012, 2 pages.

Park, "The Microbiology of Ventilator-Associated Pneumonia," Respiratory Care, vol. 50, No. 6, 24 pages.

* cited by examiner

SYSTEM AND METHOD FOR DETECTING VENTILATOR-ASSOCIATED PNEUMONIA (VAP)

TECHNICAL FIELD

This disclosure relates to systems and methods for detecting ventilator-associated pneumonia (VAP).

BACKGROUND

VAP is a form of nosocomial lung infection which can become a significant complication occurring in critically ill patients who are mechanically ventilated in an intensive care unit (ICU). VAP may increase morbidity, mortality, and costs in the healthcare system. Typically, VAP is diagnosed based on clinical signs (e.g., fever), radiographic criteria, and microbiologic criteria. Diagnosis based on microbiologic criteria may use invasive endotracheal aspirates (EA), specimens obtained by bronchoalveolar lavage (BAL), or protected specimen brush (PSB). For example, samples of the lower respiratory tract may be obtained invasively when suspicion of infection is high before the antibiotic therapy is started.

However, the invasive sampling involves risk, especially in patients with severe pulmonary disease, high respiratory support settings, and coagulation abnormalities. In addition, analysis of the samples is laborious and time-consuming, which may take up to 48 hours before definite results are available. During this period of time, the patient might have received empirical broad-spectrum antibiotics as the initial antibiotic therapy. Inadequate initial antibiotic therapy may lead to excess mortality, while excessive antibiotic therapy may increase treatment-related complications and costs, and lead to increased prevalence of antibiotic resistance. In the ICU setting where a rapid emergence and dissemination of multi-drug resistant microorganisms is particularly a concern, strategies to reduce the general and non-targeted antibiotic consumption are very important. As such, a non-invasive method that can detect the precursors of VAP at an early stage of a disease process (e.g., bacterial infiltrates/colonization) is generally desired.

SUMMARY

In one embodiment, the present disclosure provides a processing system for detecting precursors of VAP in a patient being ventilated. The processing system comprises a memory and a processor operably connected to the memory. The memory stores a baseline value for a content of a particular volatile organic compound (VOC) in the totality of multiple volatile organic compounds (tVOCs) in exhaled breath of the patient being ventilated and a trending log including values of the content of the particular VOC in the tVOCs measured at various points of time. The processor is configured to trend changes of the values of the content of the particular VOC in the tVOCs measured at various points of time compared to the baseline value, determine whether the patient has potentially infected VAP based at least in part on the trending, and in response to determining that the patient has potentially infected the VAP, generate an alert.

In another embodiment, the present disclosure provides a method for facilitating the diagnosis of VAP in a patient. The method comprises determining whether clinical presentation of the patient suggests VAP infection, in response to determining that the clinical presentation of the patient does not suggest VAP infection, determining whether a trend of a particular VOC in tVOCs of the patient suggests VAP infection, in response to determining that the trend suggests VAP infection, determining whether a recent chest radiograph of the patient is abnormal, and in response to determining that the recent chest radiographs is abnormal, recommending further diagnosis and/or treatment directed to VAP.

In yet another embodiment, the present disclosure provides a method for detecting precursors of VAP in a patient being ventilated. The method comprises obtaining a baseline value for a content of a particular VOC in tVOCs in exhaled breath of the patient being ventilated, trending changes of values of the content of the particular VOC in the tVOCs measured at various points of time after ventilation compared to the baseline value, determining whether the patient has potentially infected VAP based at least in part on the trending, and in response to determining that the patient has potentially infected the VAP, generating an alert.

BRIEF DESCRIPTION OF THE DRAWINGS

Various aspects of this disclosure may be better understood upon reading the following detailed description and upon reference to the drawings in which.

The drawings illustrate specific aspects of the described systems and methods for non-invasively detecting VAP in patients. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of systems and methods for non-invasively detecting VAP in patients. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide systems and methods for non-invasively detecting precursors of VAP in patients. An exemplary method monitors the content of a particular volatile organic compound (e.g., ethanol) in the totality of multiple volatile organic compounds (tVOCs) in the exhaled breadth of a patient during mechanical ventilations. In some embodiments, the tVOCs are inclusive of alcohols, aromatics, aldehydes, esters, ketones and terpenes in the exhaled breath of a patient during mechanical ventilation. In some embodiments, the VOCs under consideration for tVOC sensing include 2-methylbutane, heptane, dodecane and tetradecane (alkanes), carane (hydrocarbon ring structure), ethanol and isopropyl alcohol (alcohols), acrolein and tetradecanal (aldehydes), acetone (ketone), ethylbenzene (aromatic hydrocarbon) and tetrahydrofuran (oxygen-containing heterocyclic compound).

The method provides an early indication of potential infection of VAP prior to clinical manifestation based on the trending of the content of the particular VOC in the tVOCs. VOCs are mainly blood borne and therefore reflect different processes in the body. Thus, data of the exhaled VOC/tVOC(s) provide useful information to clinicians caring for the ICU patients. For example, VOCs such as ethanol, can be produced at an increased level by bacteria in VAP positive patients as a metabolite end-product. In an exemplary method, the content of a particular VOC (e.g., ethanol) in the tVOCs in the exhaled breath of a patient was measured shortly after the patient was initially intubated (e.g., first hour post-intubation) and stored as a baseline value. As the mechanical ventilation continues, the content of the particular VOC in the tVOCs (i.e., VOC/tVOCs) is monitored and trended over the time. If the trending indicates an increase of VOC/tVOCs, possibly caused by bacterial infection, an alert of potential VAP may be generated. As such, a simple, safe, and non-invasive method is provided to indicate possible bacterial lung infection at an early stage (e.g., within the 48-hour window), which potentially leads to an early diagnosis and treatment plan.

In some embodiments, the trending of VOC/tVOCs can be used in combination with other physiological parameter(s) (e.g., heart rate, temperature) of the patient to diagnose VAP and/or initiate the cascade of subsequent interventions. For example, the ratio of arterial oxygen partial pressure to fractional inspired oxygen (PaO2/FiO2) of a patient can be monitored during the mechanical ventilation. The ratio of PaO2/FiO2 may drop 12-24 hours before the clinical manifestation of VAP. A decline in the PaO2/FiO2 and an increase of VOC/tVOCs (e.g. ethanol, etc.) may be used in combination to diagnose VAP.

In some embodiments, the trending of VOC/tVOCs may be incorporated into another workflow of diagnosing and/or treating VAP. For example, an existing workflow uses clinical features, radiographic criteria, and/or microbiological criteria to diagnose VAP. The VOC/tVOCs trending can be used to verify/strengthen the clinical features and radiographic criteria before the microbiological criteria being applied.

In some embodiments, a more targeted administration of antibiotic therapy may be conducted based on the trending of VOC/tVOCs. For example, if the trending of VOC/tVOCs indicates potential VAP during the first 48 hours of mechanical ventilation, this early-onset VAP may be caused by less severe bacteria such as Staphylococcus aureus, Streptococcus pneumoniae and Haemophilus influenza which are all anti-biotic sensitive. Empirical broad-spectrum antibiotic therapy may be prescribed. If the trending of VOC/tVOCs indicates a late onset VAP that takes place more than 72 hours post-intubation, the infection may be caused by multidrug resistant pathogens such as Pseudomonas aeruginosa, Acinetobacter and Stenotrophomonas. Antibiotic therapy may be directed to these types of bacteria. In further embodiments, monitoring of VOC/tVOCs continues during the course of the antibiotic therapy, which can indicate the effectivity of the antibiotic therapy non-invasively.

Figure 1A:
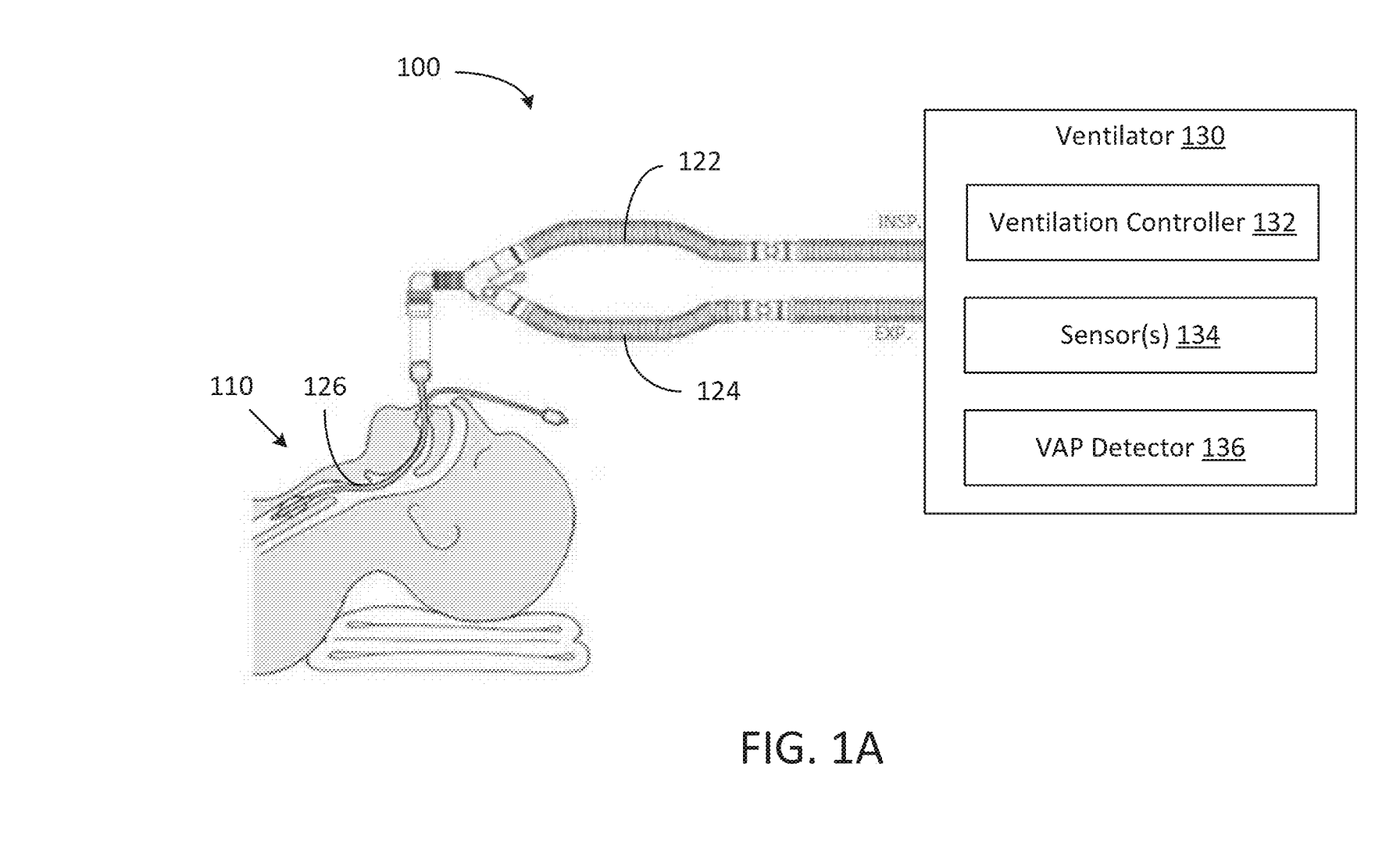
FIG. 1A is a schematic diagram of the environment for detecting precursors of VAP, in accordance with an exemplary embodiment.

Now referring to FIG. 1A, a schematic diagram of the environment 100 for non-invasively detecting VAP in a patient is shown, in accordance with an exemplary embodiment. As illustrated in FIG. 1A, in some embodiments, the environment 100 comprises a ventilator 130 working on a patient 110. The ventilator 130 may be a stand-alone ventilator or may be a part of an anesthesia delivery system. The ventilator 130 is configured to deliver ventilation gas to the patient 110 through an inspiratory branch 122 and a tracheal tube 126 placed into the trachea of the patient 110. Exhaled gases are removed from the patient 110 through the tracheal tube 126 and an expiratory branch 124.

The ventilator 130 comprises a ventilation controller 132, one or more sensor(s) 134, and a VAP detector 136. The ventilation controller 132 is configured to control the mechanical ventilation process to adapt to the needs of the patient 110. For example, the respiratory rate, fraction of inspired oxygen (FiO2), volume or pressure control, and/or ventilator mode may be set through the ventilation controller 132 based on the patient condition. In some embodiments, the ventilation controller 132 controls the ventilator 130 to apply prophylactic positive end expiratory pressure (PEEP) for non-hypoxemic ventilated patients.

The sensor(s) 134 is configured to monitor multiple volatile organic compounds (i.e., constituents of the tVOCs) in the exhaled breath of the patient 110 and provide a signal indicative of the compounds. In some embodiments, the sensor(s) 134 is configured to monitor the content of a particular VOC in the tVOCs (i.e., VOC/tVOCs) and provide a signal indicative of such. The VAP detector 136 is configured to detect precursors of the VAP based at least in part on the signal provided by the sensor(s) 134. Structure of the VAP detector 136 will be explained in detail below with reference to FIG. 2.

VOCs may be transported from different organs via blood to the lungs and subsequently excreted from there via exhaled breath. A multitude of tVOCs in the exhaled breath may originate from exogenous (e.g., environmental) and endogenous sources. Endogenous VOCs are produced by biological process (e.g., oxidative stress and inflammation) in the human body, as well as by invading microorganisms. Harmful microorganisms that invade the lungs may produce specific compounds, which may change the content of a VOC in the tVOCs (i.e., VOC/tVOCs) in the exhaled breath. In response to the microbial infection, the host may subsequently set the defense mechanism (e.g., inflammatory response) in motion, which may cause further change in the VOC/tVOCs of the exhaled breath. As such, the VOC/tVOCs of a patient with VAP may be different from that of a healthy individual.

The major in the exhaled breath of healthy individuals include isoprene (12-580 ppb), acetone (1.2-1,880 ppb), ethanol (13-1000 ppb), and methanol (160-2000 ppb). Studies show that the bacterial mechanism associated with VAP produce several discriminatory VOCs, wherein five of seven identified VAP-causing bacterial metabolic pathways generate ethanol as an end-product and one utilizes ethanol. Comparing to healthy individuals, VAP positive patients may have a higher level of ethanol concentration in the exhaled breath.

In some embodiments, the sensor(s) 134 is placed at a position in fluid communication with the expiratory branch 124 and configured to measure the ethanol concentration in the exhaled breath. The sensor(s) 134 may include any appropriate sensors of various models and/or by various manufacturers. It should be understood that although ethanol is used here as the biomarker for detecting VAP, any other appropriate VOC may be used. It should also be understood that more than one VOC may be used in combination to detect VAP, in some embodiments.

It should be understood that the ventilator 130 as shown in FIG. 1A is for illustration not for limitation. Various ventilators can be used which may have more, fewer, and/or different components as shown. For example, the ventilator may include a monitor device for displaying machine parameters, patient physiological parameters, and other information, and/or an operator interface for an operator to interact with the ventilator (e.g., adjust settings of the ventilator, respond to prompts, etc.). For example, this concept can be further extended to continuous positive airway pressures (CPAP) systems used in both professional care settings and in the consumer markets.

In some embodiments, the ventilator 130 is connected to and communicates with the patient's bed (e.g., monitoring the angle of the patient's bed/positioning of the patient), enteral nutrition pumps and/or an IT infrastructure of the hospital (e.g., central station, electronic medical record (EMR), etc.) through a communication connection. The communication connection can be implemented by any appropriate wired connection, wireless connection, or any combination therefore, such as cable, data bus, universal serial bus (USB) connection, radio frequency (RF) connection, infrared connection, optical connection, near field communication (NFC), etc.

In some embodiments, the ventilator 130 includes VAP-prevention mechanism. For example, the ventilator 130 may be configured to monitor the patient for gastric overdistention, monitor and continuously control the endotracheal tube cuff pressure to a specified minimum (e.g., 20 cm $H_2O$) or other user programmed value, and so on. Continuous control of ETT cuff pressure is important in maintaining an appropriate seal to ensure that the contents (secretions, bacteria, mucus, etc.) of the oropharyngeal area do not migrate toward the lungs, proper ventilation is achieved and there is good tracheal perfusion. It is additionally envisioned that the ETT cuff pressure controller could be used to monitor for leaks past the cuff (via. detectable flow or pressure drop), and/or communicate intelligently with the ventilator to determine breathing circuit leaks, and modulate the cuff pressure to achieve a proper tracheal seal.

Figure 1B:
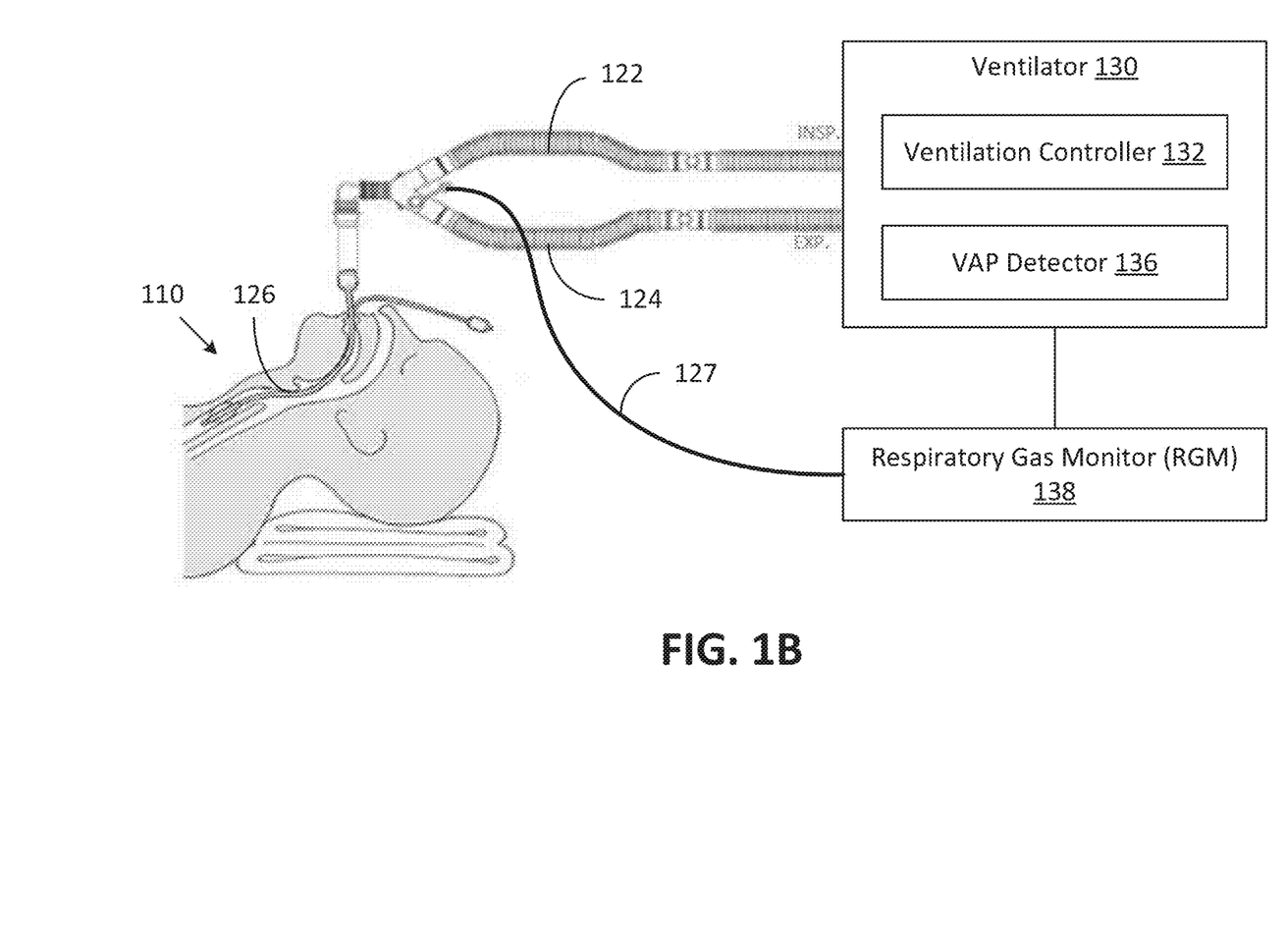
FIG. 1B is a schematic diagram of the environment for detecting precursors of VAP, in accordance with another exemplary embodiment.
Figure 1C:
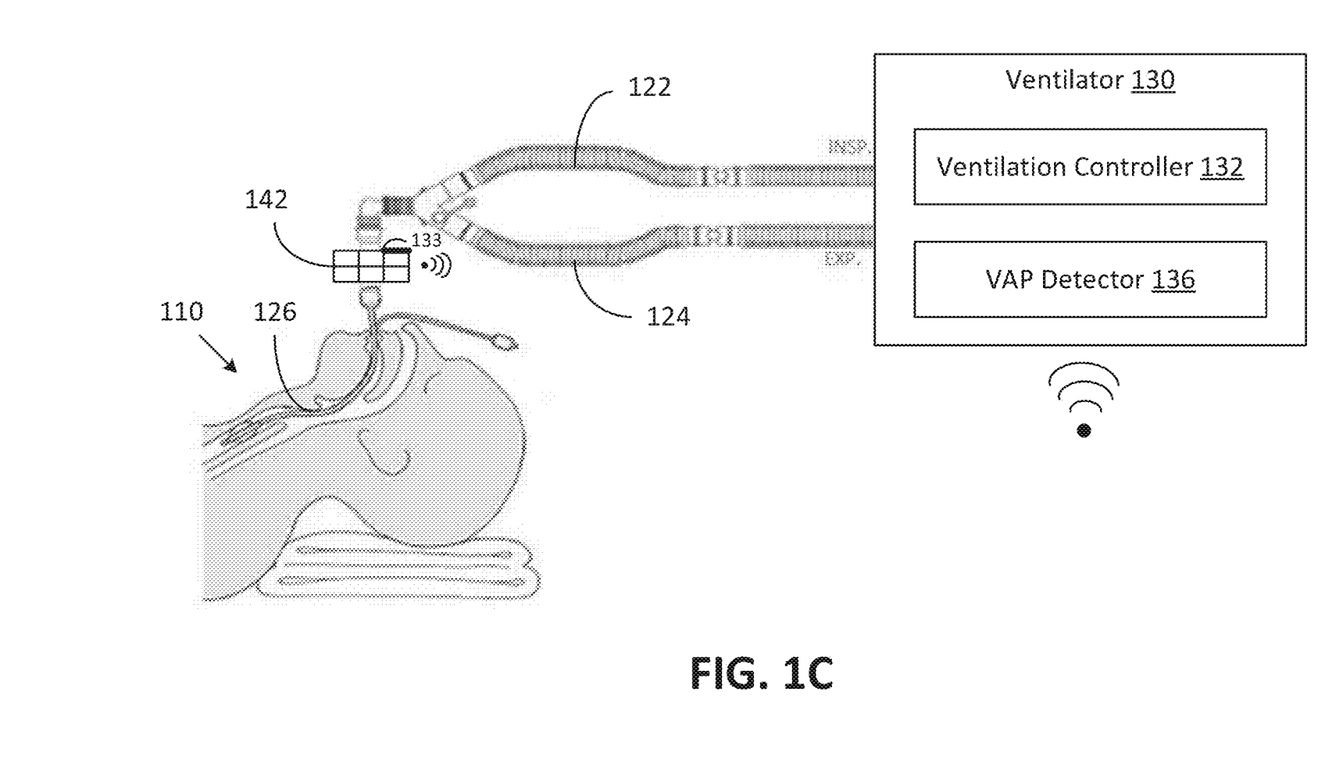
FIG. 1C is a schematic diagram of the environment for detecting precursors of VAP, in accordance with yet another exemplary embodiment.
Figure 1D:
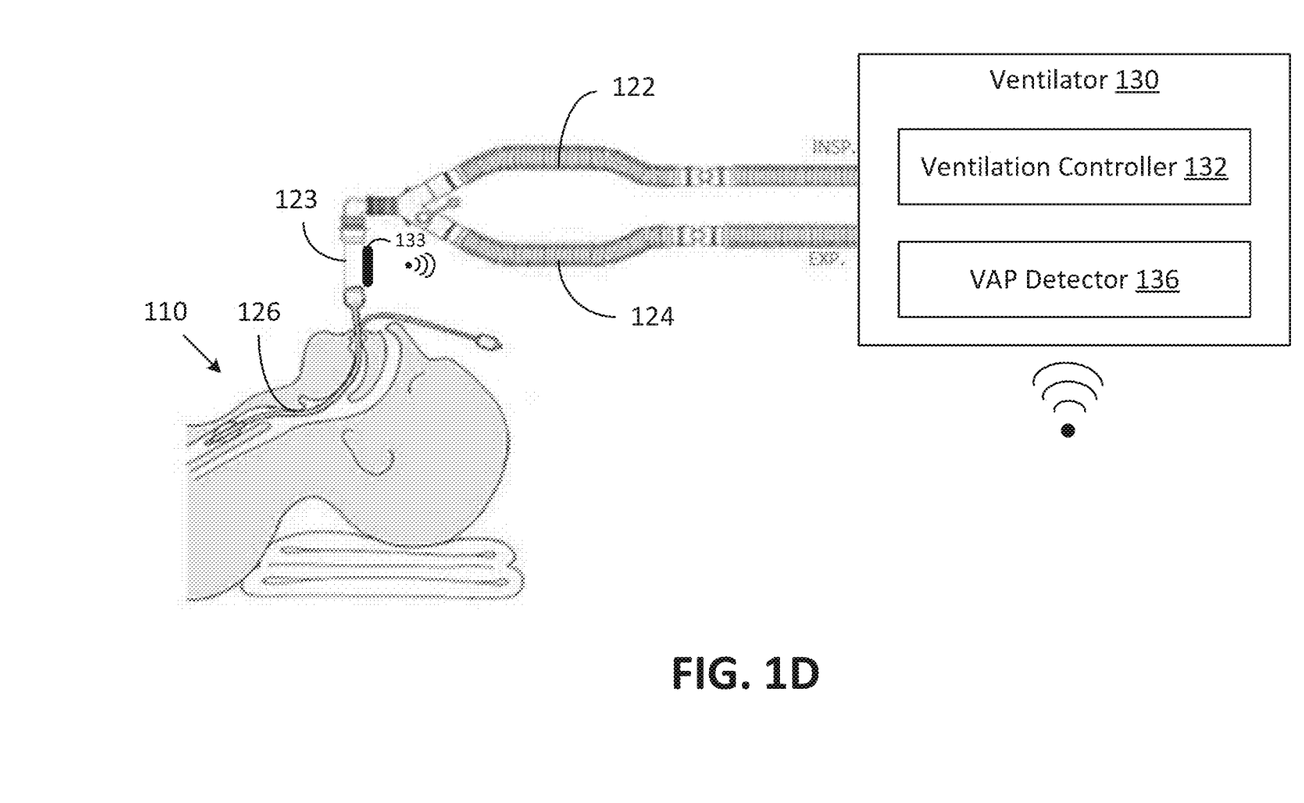
FIG. 1D is a schematic diagram of the environment for detecting precursors of VAP, in accordance with still another exemplary embodiment.

FIGS. 1B, 1C, and 1D show multiple variations of the architecture for detecting VAP in a patient, according to various embodiments. As shown in FIG. 1B, a respiratory gas monitor (RGM) 138 is in fluid communication with the expiratory branch 124 through a sample line 127 and configured to monitor the VOC/tVOCs in the exhaled breath of the patient 110. The RGM 138 is communicatively connected to the ventilator 130 to provide the VOC/tVOCs data to the ventilator 130. As shown in FIG. 1C, a wireless sensor 133 is incorporated into a patient circuit bacterial filter 142 (e.g., a heat and moisturizer exchange (HME) filter) and configured to monitor the VOC/tVOCs in the exhaled breath of the patient 110 at the exhalation valve of the filter 142. The ventilator 130 is configured to receive the VOC/tVOCs data from the sensor 133 via a wireless communication interface. As shown in FIG. 1D, in some situations where the ventilator 130 is equipped with a device for scavenging exhaust gas, the wireless sensor 133 is configured to sample the scavenging exhaust gas and monitor the VOC/tVOCs in the exhaust gas.

It should be understood that FIGS. 1A through 1D are exemplary configurations and may be not exhaustive. Any other appropriate configurations can be used herein. For example, in the situations where an ICU ventilator system uses a blow to draw in ambient room air, a separate (or multiplexed) sensor may be used to monitor the ambient air baseline VOC/tVOC(s) levels, which is then used adjust the measured VOC/tVOCs level of the exhaled breath.

Figure 2:
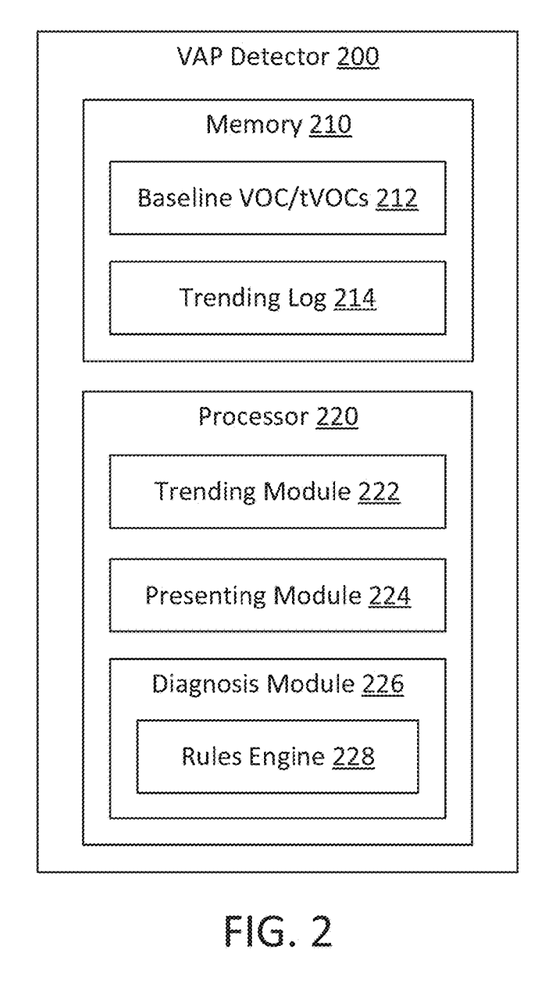
FIG. 2 is a block diagram of a VAP detector which can be used in FIGS. 1A-1D, in accordance with an exemplary embodiment.

Referring to FIG. 2, a block diagram of a VAP detector 200 is shown, in accordance with an exemplary embodiment. The VAP detector 200 may be used as the VAP detector 136 in FIGS. 1A through 1D. The VAP detector 200 may be implemented on any appropriate processing system. The processing system may include a memory 210 and processor 220. The memory 210 may be a non-transitory computer-readable medium which stores computer executable code to be processed by the processor 220 and data to be used by the processor 220 to perform the operations described herein. In some embodiments, the VAP detector 200 may be implemented on more than one processing system, i.e., a portion of the VAP detector 200 is run on one processing system, and another portion of the VAP detector 200 is run on another processing system.

As illustrated in FIG. 2, in some embodiments, the memory 210 stores a baseline VOC/tVOCs value 212 and trending log 214. The processor 220 comprises a trending module 222, a presenting module 224, and a diagnosis module 226 which includes a rules engine 228. In some embodiments, the baseline VOC/tVOCs value is the concentration of a VOC (e.g., ethanol) in the exhaled breath of the patient which was measured shortly after the patient was initially intubated (e.g., first hour post-intubation/mechanical ventilation). In some embodiments, the baseline VOC/tVOCs value 212 is an average of multiple measurements. This baseline VOC/tVOCs value 212 may be used to define an initial steady-state exhaled VOC/tVOCs and to initiate the trending log 214.

As the mechanical ventilation continues for the patient, the VOC/tVOCs in the exhaled breath of the patient is measured periodically (e.g., every minute, 5 minutes, 10 minutes, 20 minutes, and so on). In some embodiments, multiple measurements are performed after each interval and the average of the multiple measurements is recorded. The measurements of VOC/tVOCs, along with the time of measurements (e.g., the elapsed time since the start of the ventilation), may be stored in the trending log 214. The trending module 222 is configured to trend the changes in the values of the VOC/tVOCs (e.g., ethanol concentration) being monitored. In some embodiments, the change in the VOC/tVOCs value is the difference between the measured VOC/tVOCs value (in the trending log 214) at various points of time and the baseline VOC/tVOCs value.

Figure 3:
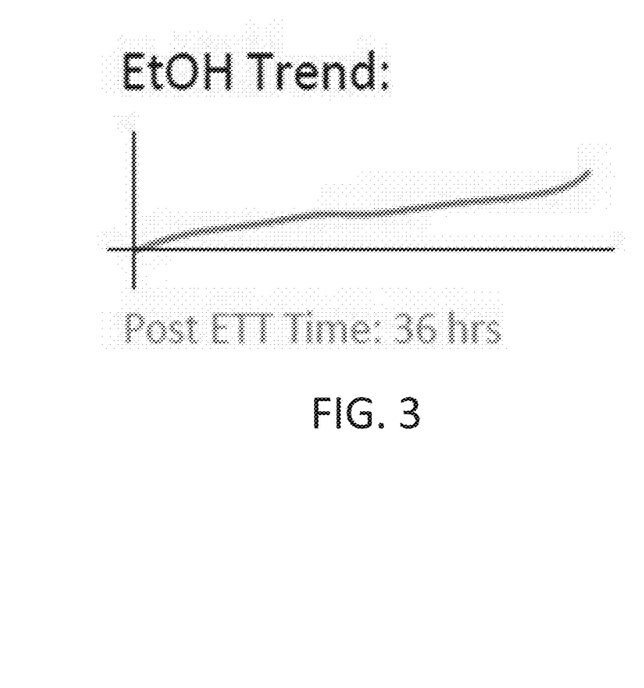
FIG. 3 is a graph of the ethanol concentration in the exhaled breath of a patient changing over time, in accordance with an exemplary embodiment.

In some embodiments, the presenting module 224 may cause a display connected with the ventilator to display the trending of the VOC/tVOCs. FIG. 3 shows a graph of the ethanol concentration in the exhaled breath of the patient changing over time, in accordance with an exemplary embodiment.

The diagnosis module 226, using the rule engine 228, determines whether the patient has potentially infected VAP based at least in part on the VOC/tVOCs trend. In some embodiments, the rules engine 228 includes rules that determines VAP infection based solely on the VOC/tVOCs trend. For example, if the VOC/tVOCs trend of the patients shows an upward pattern in a certain amount of time, it may be determined that the patient has potentially infected VAP. As an example, the ethanol concentration has doubled in 20 hours, or the increase of the concentration comparing to the baseline value has reached a predefined threshold value, which may suggest potential VAP infection. In some embodiments, the rules take into account of the risk of re-intubation—the risk of VAP may have a significant correlation to re-intubation. If the re-intubation attempts have been recorded, the rules engine 228 may set a lower threshold value for the VOC/tVOCs in these situations.

In some embodiments, in response to potential VAP being detected, the presenting module 222 generates an alert to a clinician indicating the potential infection. In some embodiments, the alert includes a visual indication (e.g., text message, flashing lights, etc.) on a display connected to the ventilator. In some embodiments, the alert is audible, comprising a tone or pre-recorded message. In some embodiments, the alert is sent to a central station and/or a user device associated with the clinician.

In some embodiments, the rules engine 228 includes rules that determines VAP infection based on the VOC/tVOCs trend in combination with other metrics of the patient. For example, the rules may take the patient demographics into consideration, including for example, age, weight (obesity), sex, race, comorbidities, history of alcoholism, smoking, chronic occupational exposure, etc. For patients of different demographics, the rules may set different threshold values of VOC/tVOCs concentration and/or different amount of time for potential VAP infection.

As another example, the rules engine 228 includes rules that use the VOC/tVOCs trend along with physiological parameters of the patient, including for example, body/core temperature, heart rate, etc. The physiological parameters may be monitored and transmitted to the ventilator through the communication connection (wired/wireless). For example, the ratio of PaO2/FiO2 of the patient may be monitored during the mechanical ventilation. If the data is communicated to the EMR system either through the lab or through a monitor, the ventilator can mine the data stream and use the data. PaO2/FiO2 may drop 12-24 hours before the clinical manifestation of VAP. If a decline in the PaO2/FiO2 and an increase of ethanol concentration have occurred, the diagnosis module 226 may determine that the patient has potentially infected VAP.

Figure 4:
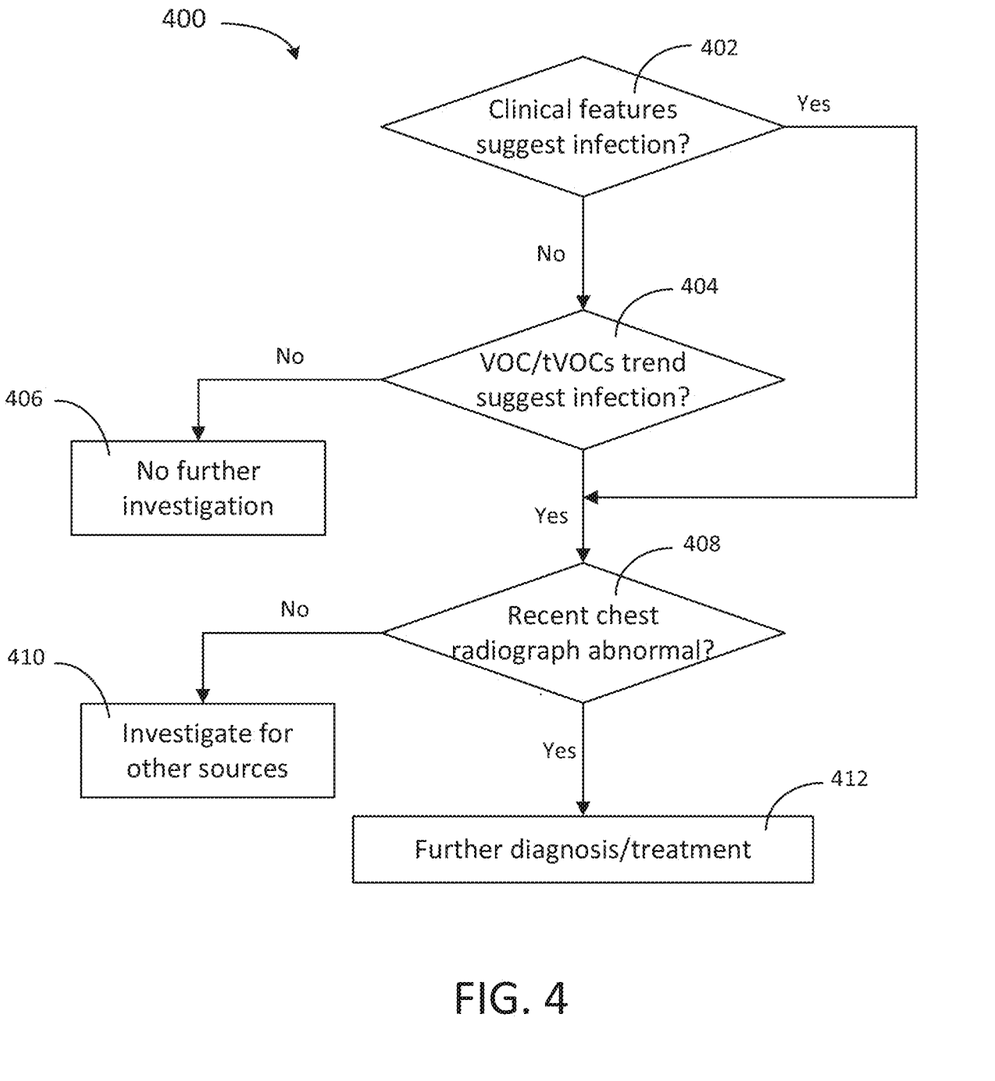
FIG. 4 is a diagram of a workflow for facilitating diagnosis of VAP, in accordance with an exemplary embodiment.

In some embodiments, the diagnosis module 226 incorporates the VOC/tVOCs trend into another workflow for diagnosing VAP that may use a combination of clinical features, radiographic criteria, and microbiological criteria. FIG. 4 shows a workflow 400 of diagnosing VAP that incorporates the VOC/tVOCs trend, in accordance with an exemplary embodiment. At an operation 402, it is determined whether clinical features suggest VAP infection. In some embodiments, the clinical features include a fever (e.g., higher than 38° C.), leukocytosis, leukopenia along with purulent discharge, and/or other appropriate features. If the clinical features do not suggest that the patient has infected VAP at operation 402, the workflow proceeds to operation 404, where it is determined whether the VOC/tVOCs trend suggests VAP infection. For example, if the VOC/tVOCs (e.g. ethanol) concentration has increased to a certain level in a certain amount of time, it may be determined that the VOC/tVOCs trend suggests VAP infection. If the VOC/tVOCs trend does not suggest VAP infection at operation 404, it is determined no further investigation is needed, at operation 406.

If the VOC/tVOCs trend suggests VAP infection (at operation 404), or if the clinical features suggest VAP infection (at operation 402), the workflow proceeds to operation 408, where it is determined whether the recent radiograph is abnormal. The abnormal radiograph may include, for example, chest radiograph or CT scan with asymmetric pulmonary infiltrates. If the recent chest radiograph is determined to be not abnormal at operation 408, other sources than VAP might have caused the clinical features or VOC/tVOCs trend and will be investigated, at operation 410. If the recent chest radiograph is determined to be abnormal at operation 408, further diagnosis and/or treatment directed to VAP infection is determined at operation 412.

In some embodiments, the presenting module 224 provides a recommendation to a clinician regarding the next step of diagnosis and/or treatment based on any combination of the clinical features, VOC/tVOCs trend, and chest radiograph. In some embodiments where the patient is clinically unstable, the recommendation may include conducting a quantitative testing, such as non-bronchoscopic testing (e.g., ETA, BAL, PSB) or bronchoscopic testing (e.g., BAL, PSB, protected BAL). Further treatment can be decided based on the results of the testing.

In some embodiments, the presenting module 224 provides a treatment recommendation including a targeted administration of antibiotic therapy based on the timing of the diagnosis of VAP infection. For example, if the VAP is diagnosed during the first 48 hours of mechanical ventilation, this early-onset VAP may be caused by less severe bacteria such as Staphylococcus aureus, Streptococcus pneumoniae and Haemophilus influenza which are all antibiotic sensitive. The prescription may include an empirical broad-spectrum antibiotic therapy. If the diagnosis shows a late onset VAP that takes place more than 72 hours post-intubation, it may be caused by multi-drug resistant pathogens such as Pseudomonas aeruginosa, Acinetobacter and Stenotrophomonas. Antibiotic therapy may target at these types of bacteria.

In further embodiments, monitoring of the VOC/tVOCs continues during the course of the antibiotic therapy, which can indicate the effectivity of the antibiotic therapy non-invasively. For example, if the ethanol concentration has not dropped to a predefined value during certain amount of time, the antibiotic therapy might be inefficient and the clinician may consider adjusting the therapy.

It should be understood that the workflow as shown in FIG. 4 is for illustration not for limitation. An appropriate workflow incorporating VOC/tVOCs trend in VAP diagnosis may include more, fewer, or different operations than those shown in FIG. 4.

Figure 5:
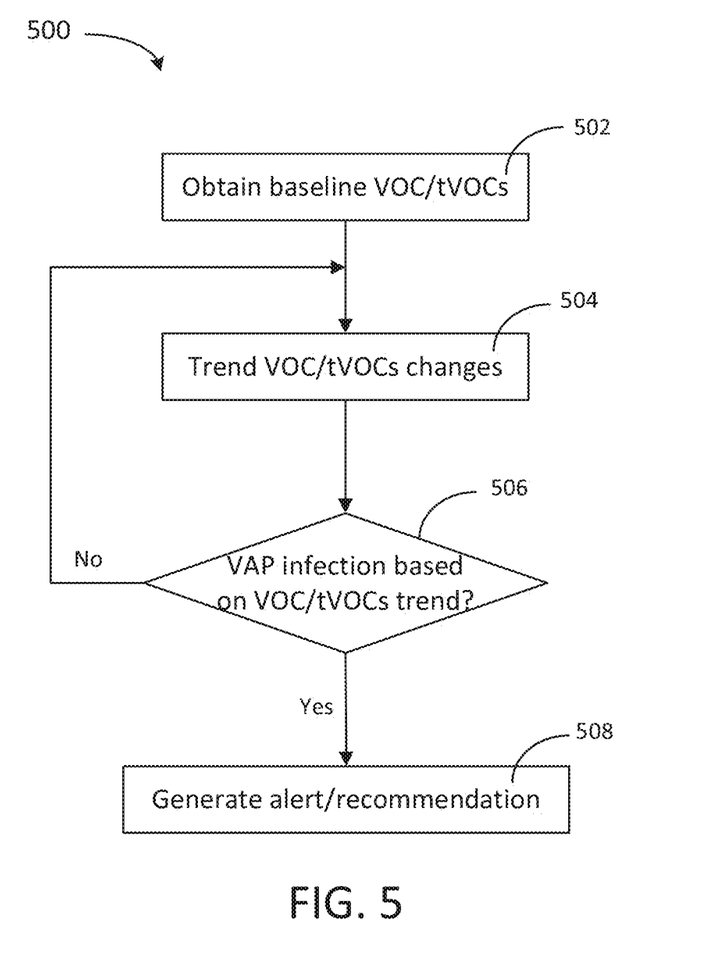
FIG. 5 is a flow chart of a method for detecting precursors of VAP, in accordance with an exemplary embodiment.

Referring to FIG. 5, a flow chart 500 of a method for detecting VAP in a patient is shown, in accordance with an exemplary embodiment. The method can be executed by the VAP detector 136 in FIGS. 1A through 1D and the VAP detector 200 in FIG. 2. At an operation 502, a baseline VOC/tVOCs value is obtained. In some embodiments, the baseline VOC/tVOCs value is the content of particular VOC(s) (e.g., ethanol) in the tVOCs in the exhaled breath of the patient which was measured shortly after the patient was initially intubated (e.g., first hour post-intubation/mechanical ventilation). In some embodiments, the baseline VOC/tVOCs value is an average of multiple measurements. This baseline VOC/tVOCs value defines an initial steady-state exhaled VOC/tVOCs concentration.

At an operation 504, changes in the monitored VOC/tVOCs (e.g., ethanol concentration) is trended over the time. As the mechanical ventilation continues for the patient, the VOC/tVOCs (e.g., ethanol concentration) in the exhaled breath of the patient is periodically measured and changes are trended. In some embodiments, a graph of the VOC/tVOCs trend (e.g., the graph in FIG. 3) is displayed.

At an operation 506, it is determined whether the patient has potentially infected VAP based at least in part on the VOC/tVOCs trend. In some embodiments, the infection is diagnosed solely based on the VOC/tVOCs trend. For example, if the VOC/tVOCs trend shows certain upward pattern in a certain amount of time (e.g., the VOC/tVOCs has doubles in 20 hours, the increase has reaches a predefined threshold value, etc.), it is determined that the patient has potentially infected VAP. In some embodiments, the diagnosis takes into account of the risk of re-intubation. If the re-intubation attempts were recorded, the threshold value of VOC/tVOCs concentration for VAP infection may be reduced.

In some embodiments, the VAP is diagnosed using the VOC/tVOCs trend in combination with other metrics of the patient. In some embodiments, the patient demographics are taken into consideration, including for example, age, weight (obesity), sex, race, comorbidities, history of alcoholism, smoking, chronic occupational exposure, etc. Different threshold values of VOC/tVOCs concentration for VAP infection can be set for patients of different demographics. In some embodiments, other physiological parameters of the patient are used in combination with VOC/tVOCs trend, including for example, body/core temperature, heart rate, etc. In some embodiments, the VOC/tVOCs trend is incorporated into another workflow for diagnosing VAP, as shown in the workflow of FIG. 4. The diagnosis may use the VOC/tVOCs trend with any combination of clinical features and radiographic criteria before the invasive microbiological test being applied.

If it is determined at operation 506 that the patient has not infected VAP, the method continues to trend the VOC/tVOCs changes. If it is determined at operation 506 that the patient has potentially infected VAP, an alert is generated to indicate the potential infection at operation 508. The alert may include any combination of a visual indication (e.g., text message, flashing lights, etc.), an audible indication (e.g., a tone or pre-recorded message), presented locally and/or remotely.

In some embodiments, a recommendation is generated regarding the next step of diagnosis and/or treatment based on any combination of the clinical features, VOC/tVOCs trend, and chest radiograph. In some embodiments, the recommendation includes conducting a quantitative testing, such as non-bronchoscopic testing (e.g., ETA, BAL, PSB) or bronchoscopic testing (e.g., BAL, PSB, protected BAL). Further treatment can be decided based on the results of the testing. In some embodiments, the recommendation includes a targeted administration of antibiotic therapy based on the timing of diagnosis of VAP infection. In further embodiments, the VOC/tVOCs monitoring continues during the course of the antibiotic therapy, which can indicate the effectivity of the antibiotic therapy non-invasively.

It should be understood that the process as shown in FIG. 5 is for illustration not for limitation. An appropriate process may include more, fewer, or different operations than those shown in FIG. 5.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A processing system for detecting precursors of ventilator-associated pneumonia (VAP) in a patient being ventilated, the processing system comprises:
   a memory storing:
   a baseline value for a content of a particular volatile organic compound (VOC) in the totality of multiple Volatile Organic Compounds (tVOCs) in exhaled breath of the patient being ventilated; and
   a trending log including values of the content of the particular VOC in the tVOCs measured at various points of time; and
   a processor operably connected to the memory and configured to:
   trend changes of the values of the content of the particular VOC in the tVOCs measured at various points of time compared to the baseline value;
   determine whether the patient potentially has infection-based VAP based at least in part on the trending, wherein the determining whether the patient potentially has the infection-based VAP comprises adjusting a predefined threshold value indicating the infection-based VAP in response to determining that the patient was re-intubated; and
   in response to determining that the patient potentially has the infection-based VAP, generate a recommendation indicating a diagnosis, a treatment, or a combination thereof.

2. The processing system of claim 1, wherein the baseline value for the content of the particular VOC in the tVOCs includes a content of ethanol in the tVOCs in the exhaled breath of the patient measured during the first hour of ventilation.

3. The processing system of claim 1, wherein the determining whether the patient has infection-based VAP comprises:
comparing an increase of the values of the content of the particular VOC in the tVOCs in a predefined amount of time with the predefined threshold value; in response to the increase being greater than the predefined threshold value, determining that the patient has the infection-based VAP.

4. The processing system of claim 1, wherein the determining whether the patient potentially has the infection-based VAP comprises:
determining whether the trend of the content of the particular VOC in the tVOCs suggests VAP infection;
determining whether another physiological parameter is abnormal; and
in response to determining the trend suggests VAP infection and the another physiological parameter is abnormal, determining that the patient potentially has the infection-based VAP.

5. The processing system of claim 1, wherein the determining whether the patient potentially has the infection-based VAP comprises incorporating the trending of the content of the particular VOC in the tVOCs into another workflow for diagnosing VAP.

6. The processing system of claim 1, wherein the recommendation includes a targeted administration of antibiotic therapy based on a timing of diagnosis of the infection-based VAP.

7. The processing system of claim 1, wherein the processor is further configured to:
continue to trend the changes of the values of the content of the particular VOC in the tVOCs measured after an antibiotic therapy is applied on the patient; and determine efficiency of the antibiotic therapy based on the trending.

8. A method for facilitating diagnosis of VAP in a patient, the method comprising:
determining whether clinical presentation of the patient suggests VAP infection, wherein the determining whether the patient potentially has the VAP infection comprises adjusting a predefined threshold value indicating the VAP infection in response to determining that the patient was re-intubated;
in response to determining that the clinical presentation of the patient does not suggest VAP infection, determining whether a trend of a content of a particular VOC in tVOCs of the patient suggests VAP infection; in response to determining that the trend suggests VAP infection, determining whether a recent chest radiograph of the patient is abnormal; and in response to determining that the recent chest radiograph is abnormal, recommending diagnosis, a treatment, or a combination thereof, directed to the VAP infection.

9. The method of claim 8, wherein the clinical features comprise at least some of fever, leukocytosis, and leukopenia along with purulent.

10. The method of claim 8, wherein the trend of the patient includes a trend of changes of ethanol content in the tVOCs in exhaled breath of the patient measured at various points of time after ventilation.

11. A method for detecting precursors of VAP in a patient being ventilated, the method comprises:
obtaining a baseline value for a content of a particular VOC in the tVOCs in exhaled breath of the patient being ventilated;
trending changes of values of the content of the VOC in the tVOCs measured at various points of time after ventilation compared to the baseline value;
determining whether the patient potentially has infection-based VAP based at least in part on the trending, wherein the determining whether the patient potentially has the infection-based VAP comprises adjusting a predefined threshold value indicating the infection-based VAP in response to determining that the patient was re-intubated; and
in response to determining that the patient potentially has the infection-based VAP, generating a recommendation indicating a diagnosis, a treatment, or a combination thereof.

12. The method of claim 11, wherein the baseline value for the content of the particular VOC includes a content of ethanol in the tVOCs in the exhaled breath of the patient measured during the first hour of ventilation.

13. The method of claim 11, wherein determining whether the patient potentially has the infection-based VAP comprises:
comparing an increase of the values of the content of the particular VOC in the tVOCs in a predefined amount of time with the predefined threshold value;
in response to the increase being greater than the predefined threshold value, determining that the patient potentially has the infection-based VAP.

14. The method of claim 13, wherein the predefined threshold value is determined based on demographics of the patient.

15. The method of claim 11, wherein the determining whether the patient potentially has the infection-based VAP comprises:
determining whether the trend of the content of the particular VOC in the tVOCs suggests VAP infection;
determining whether another physiological parameter is abnormal; and
in response to determining the trend suggests VAP infection and the another physiological parameter is abnormal, determine that the patient potentially has the infection-based VAP.

16. The method of claim 11, wherein the determining whether the patient potentially has the infection-based VAP comprises incorporating the trending of into another workflow for diagnosing VAP.

17. The method of claim 11, wherein the recommendation includes a targeted administration of antibiotic therapy based on a timing of diagnosing VAP infection.

18. The method of claim 11, further comprising:
continuing to trend the changes of the values of the content of the particular VOC in the tVOCs measured after an antibiotic therapy is applied on the patient; and
determining efficiency of the antibiotic therapy based on the trending.

* * * * *